United States Patent [19]
Stuchlik et al.

[11] Patent Number: 6,106,860
[45] Date of Patent: Aug. 22, 2000

[54] CYCLOSPORIN FORMULATION

[75] Inventors: Milan Stuchlik; Tomáš Andrýsek, both of Opava; Alexandr Jegorov, Ceske Budejovice; Ales Husek, Opava; Vladimir Matha, Ceske Budejovice; Josef Stuchlik, Hrabyne; Kvetoslava Benesova, Opava, all of Czech Rep.

[73] Assignee: Galena AS, Opava, Czech Rep.

[21] Appl. No.: 09/230,695

[22] PCT Filed: Jul. 31, 1997

[86] PCT No.: PCT/GB97/02079

§ 371 Date: Jun. 1, 1999

§ 102(e) Date: Jun. 1, 1999

[87] PCT Pub. No.: WO98/05309

PCT Pub. Date: Feb. 12, 1998

[30] Foreign Application Priority Data

Aug. 1, 1996 [CZ] Czech Rep. ............... 2289/96

[51] Int. Cl.[7] .................. A61K 9/14; A61K 9/48
[52] U.S. Cl. ............ 424/456; 424/451; 424/452; 424/453; 424/455; 424/489; 514/785
[58] Field of Search ................... 424/451, 456, 424/452, 453, 455, 489

[56] References Cited

FOREIGN PATENT DOCUMENTS

| 4322826 A1 | 1/1995 | Germany . |
| 97/26003 | 7/1997 | WIPO . |

*Primary Examiner*—James M. Spear
*Attorney, Agent, or Firm*—Beyer Weaver & Thomas, LLP

[57] ABSTRACT

Provided are therapeutic compositions which provide high bioavailability of the active ingredients from the group of cyclosporin, at the same time permitting concentrations in dosage forms higher than 10%.

9 Claims, 1 Drawing Sheet

CYCLOSPORIN FORMULATION

This application is a 371 of PCT/GB97/02079 filed Jul. 31, 1997.

This application is made under the provision of 35 U.C.S. §371.

BACKGROUND OF THE INVENTION

The invention relates to pharmaceutical formulations including, as the active ingredient, a therapeutically active cyclosporin.

Cyclosporins are a group of monocyclic, poly-N-methylated undecapeptides, which are naturally produced as secondary metabolites by certain fibrous fungi, especially of genera Tolypocladium and Cylindroqarpon. Some therapeutically useful cyclosporins can be prepared by partial synthesis or by special fermentation procedures.

Ciclosporin (Cyclosporin A) is the first natural substance having selective immunosuppressive effect on lymphoid cells, especially T lymphocytes. It also influences functions of other cells of the immune system to a great extent.

Therapy makes use especially of effects of systemically administered cyclosporins in organ transplantations or transplantations of bone-marrow. They can be employed as well for treating a wide variety of autoimmune diseases with inflammatory etiology and as anti-parasitic agents.

Certain cyclosporins without immunosuppressive activity exhibit an inhibitor effect towards replication of the HIV-1 virus and can be employed in therapy for treatment and prevention of AIDS or AIDS related complex. The group of cyclosporins includes also chemomodulators useful for influencing cross resistance of tumor cells to cytostatics.

Bioavailability of cyclosporins in the organism is influenced, on one hand, by specific properties of this group of substances, but also by the composition and properties of the particular dosage form. An important role in formulating therapeutic compositions containing cyclosporins is played by their high lipophilicity.

Solubility of these active substances in water typically does not exceed 2.5 mg/100 ml, which value is approximately 100 times lower than needed for regular absorption in the organism. The marked lipophilicity of cyclosporins is evidenced by the values of their partition coefficients P in the system n-octanol/water. For ciclosporin, values of log P=21.08 to 2.99 have been reported.

To achieve acceptable bioavailability of cyclosporins, especially those formulations are used in practice and are patented which form, when needed, dispersion systems characterised by the presence of a hydrophilic phase, a hydrophobic phase and a tensoactive component. The resulting dispersions are either classic emulsions or optically transparent microemulsions. Commercially available compositions for oral administration, known under the trade names Sandimunn®, Sandimunn®-Neoral, Consupren®, Implanta®, Imusporin® as described in GB 2015339, GB 2222770, GB 2270842, GB 2278780 and equivalents are based on this general principle.

Modifications of the preceding systems, where the hydrophilic base is omitted and replaced by partial esters of fatty acids with polyols like propylene glycol, glycerol or sorbitol, are described in GB 2228198.

German patent application DE 4322826 discloses, as the carrier system for drugs poorly soluble in water, a composition containing polyglyceryl esters of fatty acids as a co-tenside to non-ionic tensides having HLB higher than 10, in the presence of a triacyl glycerol as the lipophilic component.

Formulations containing cyclosporins in a vehicle comprising propylene glycol, mixed mono-, di- and triglyceride and a hydrophilic tenside, disclosed in GB patent 2248615, are typical microemulsion preconcentrates of the oil-in-water type.

A reverse "water-in-oil" type of the microemulsion preconcentrate containing cyclosporins defined as $L_2$ phase is disclosed in SE 95024725.

Commercially available oral cyclosporin compositions are provided as solutions or in soft gelatin capsules. Disadvantages of solution formulations provided as self-emulsifying concentrates for dilution when needed are poor patient acceptability and toxicity concerns.

Soft gelatin capsules mask the taste of the contents, but their preparation is expensive and requires special packing to avoid migration of ethanol through the wall of the capsule into the packing environment.

Some solvents for example propylene glycol, low-molecular polyethylene glycols, diethyleneglycol monoethyl ether, tetrahydrofurfuryl alcohol ether, which may be present in the contents or fill of the soft gelatin capsules, are liable to migrate into the capsule shell. Such capsules are not stable, because the shells tend to soften due to migrating solvents. Consequently the capsules may be deformed due to reduction of the volume of the contents and decrease of the pressure inside the capsule. An approach to solve these problems disclosed in GB-A-2282586 consists in adding solvents able to migrate into the capsule shell followed by reduction of the resulting tackiness of the gelatin by cooling during production.

This invention is directed to therapeutic compositions which provide high bioavailability of the active ingredients from the group of cyclosporin, at the same time permitting concentrations in dosage forms higher than the usual 10%.

The aim of this invention is to omit polar solvents in the therapeutic compositions in order to avoid the previously described undesirable effects.

According to the present invention a pharmaceutical composition for internal use, contains, as the active ingredient, 10 to 25% by weight of a cyclosporin, and a carrier composed of (i) one or more partial esters of $C_6$ to $C_{22}$ fatty acids with a glycerol derivative selected from: diglycerol to decaglycerol and (ii) partial esters of $C_8$ to $C_{16}$ fatty acids with pentaglycerol to pentadecaglycerol in mutual weight ratios (i):(ii) of 1:1 to 1:5, optionally containing additional adjuvants.

DETAILED DESCRIPTION OF PREFERRED EMBODIMENTS

Figure 1:
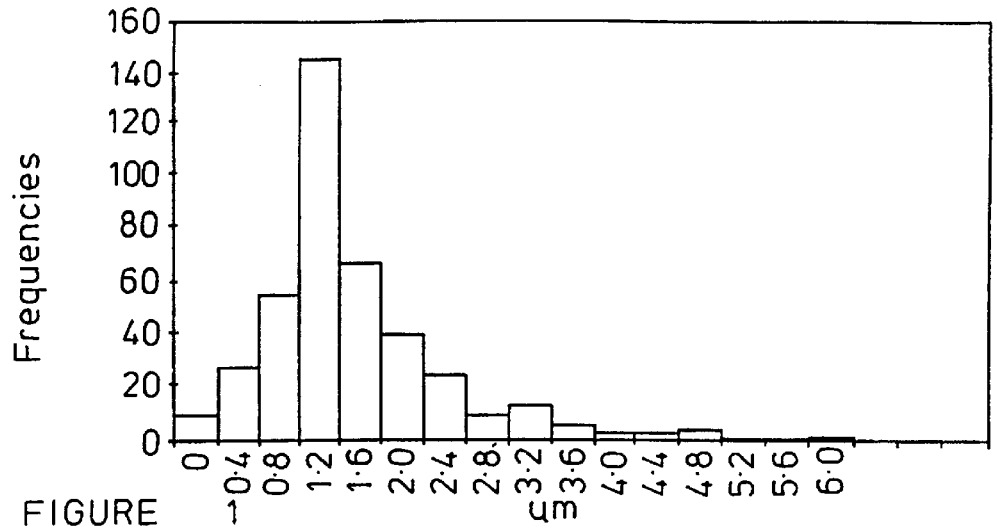
FIGS. 1, 2 and 3 illustrate histograms of particle frequencies and sizes resulting form the experiments described in Example 2.

It should be understood for the purposes of this description that a "carrier" means a pharmaceutic adjuvant in which the active substance is dissolved or dispersed in an absorbable form. When required the carrier can also contain further excipients such as antioxidants, taste correcting agents and the like.

The formulations according to this invention can be liquid at the ambient temperature or can be prepared as solids with the use of carriers having a melting point above ambient temperature. The ingredients of the carrier can be mixed together with the active substance at temperatures above the melting point before cooling to a temperature suitable for grinding to powdery granules for further treatment, eg for filling into bipartite capsules or sachets for dispersing as required. The liquid formulations, due to their viscous character, may be employed especially for filling into bipartite capsules. The capsules can then be treated, eg with an acid-resistant coating, for use in treatment of auto-immune diseases of the intestinal tract.

The partial esters of polygylcerol with fatty acids used as components of the carrier may have the general formula

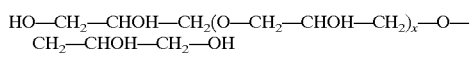

HO—CH$_2$—CHOH—CH$_2$(O—CH$_2$—CHOH—CH$_2$)$_x$—O—CH$_2$—CHOH—CH$_2$—OH wherein x=0 to 13. Preferred partial esters are characterised by the following data:

|  | mol.weight | Number of OH groups | hydroxyl value |
|---|---|---|---|
| diglycerol | 166 | 4 | 1352 |
| triglycerol | 240 | 5 | 1169 |
| tetraglycerol | 314 | 6 | 1071 |
| pentaglycerol | 388 | 7 | 1012 |
| hexaglycerol | 462 | 8 | 970 |
| heptaglycerol | 536 | 9 | 941 |
| octaglycerol | 610 | 10 | 920 |
| nonaglycerol | 684 | 11 | 903 |
| decaglycerol | 758 | 12 | 880 |
| pentadecaglycerol | 1228 | 17 | 846 |

Fatty acids suitable for esterification of polyglycerol include, pure non-branched saturated and unsaturated fatty acids as well as mixtures of fatty acids obtained by hydrolysis from natural fats and oils. The acids may also be substituted, for example 1,2-hydroxyoleic acid, or branched, for example isostearic acid.

Partial esters of polyglycerols with the $C_8$ to $C_{22}$ fatty acids are generally prepared either by esterification of polyglycerols with corresponding saturated or unsaturated acids or by trans-esterification of vegetable oils with polyglycerols. Each individual partial ester of polyglycerols may be characterised by its saponification number.

The degree of polymerisation may be indicated by the hydroxyl value. Products which are especially suitable as component (i) of the carrier include:

| diglyceryl monooleate | NIKKO ® DGMO-90 |
|---|---|
| triglyceryl monooleate | DANISCO TS-T 122 |
| tetraglyceryl monostearate | NIKKO ® Tetraglyn 1-S |
| tetraglyceryl monooleate | NIKKO ® Tetraglyn 1-0 |
| decaglyceryl trioleate | NIKKO ® Decaglyn 3-0 |
| decaglyceryl tristearate | NIKKO ® Decaglyn 3-S |
| decaglyceryl pentaoleate | NIKKO ® Decaglyn 5-0 |

Preferred compounds which may be used as component (ii) of the carrier include:

| hexaglyceryl monolaurate | NIKKO ® Hexaglyn 1-L |
|---|---|
| hexaglyceryl monococoate | — |
| hexaglyceryl monomyristate | NIKKO ® Hexaglyn 1-M |
| decaglyceryl monolaurate | NIKKO ® Decaglyn 1-L |
| decaglyceryl monomyristate | NIKKO ® Decaglyn 1-M |

Preferred components (i) of the carrier are lipophilic fat-like substances (pseudo-lipids). They have very low toxicity. The acceptable daily dose (ADI) for the polyglycerols was determined by FAO/WHO in 1975 as 25 mg/kg body weight. That is ten times greater than the acceptable dose for fatty acid microesters, which are suggested as a carrier for cyclosporin formulations in GB patent 2230440. Components (i) of the carrier include partial esters of long chain fatty acids. They dissolve the active substances well and are needed for absorption of cyclosporins from the gastrointestinal tract by the mechanism of formation of mixed micelles, in which bile acids are involved.

Preferred components (ii) include medium to long chain fatty acids. They may have an amphiphilic character, but retain their ability to dissolve cyclosporins. These acids may effect the surface tension of the mixed carrier and facilitate dispersion of the resulting combination in water. Even with a great excess of water these acids may form a physically stable dispersion having an average particle size below 2 μm. This is a preferred condition for uniform absorption of the active substance. The products of hydrolysis of partial esters of medium long fatty acids with glycerols are absorbed by another mechanism even in the absence of bile acids. That is especially advantageous in some diseases with reduced release of bile.

The whole group of the especially preferred partial esters of fatty acids with polyglycerols, useful as the carriers of the active substance, is characterised by one or more of the following criteria:

| | |
|---|---|
| acid number | max. 6 |
| fatty acid Na salts content | max. 2% (as Na stearate) |
| heavy metal content | max. 10 ppm |
| water content | max. 2% |
| total ash | max 1% |
| iodine number | 50–110 (unsaturated acid esters) |
| | max. 3 (saturated acid esters) |
| saponification number | 100–180 |

Polyglyceryl esters of fatty acids are physiologically more acceptable. adjuvants in comparison with polyoxyethylated tensides, which are commonly used in commercially available ciclosporin compositions. They do not contain any residues of ethylene oxide monomer or its conversion products such as 1,4-dioxane.

The invention is further described by means of example but not in any limitative sense with reference to the accompanying drawings of which FIGS. 1, 2 and 3 depict histograms of particle frequencies and sizes in a composition of Example 2. The horizontal axis shows particle size in pm and the vertical axes show frequencies of the corresponding particles.

EXAMPLE 1

Hard Gelatin Capsules

A formulation was prepared using the following ingredients:

| | |
|---|---|
| ciclosporin | 16.00 kg |
| diglyceryl dioleate | 24.00 kg |
| decaglyceryl monomyristate | 60.00 kg |

In a Frymix processing device, the diglyceryl dioleate was mixed with decaglyceryl myristate at 60° C. Ciclosporin was added and mixing in an evacuated vessel was continued until dissolution occurred. The warm product was filtered and filled into hard gelatin capsules in amounts corresponding to 100 mg, 50 mg and 25 mg of the active ingredient, resp., on a Zanussi AZ-40 machine.

EXAMPLE 2
Hard Gelatin Capsules

A formulation was prepared using the following ingredients:

| | |
|---|---|
| ciclosporin | 14.30 g |
| diglyceryl monooleate | 33.36 g |
| decaglyceryl monolaurate | 52.37 g |

In a jacketed glass vessel, the diglyceryl monooleate was mixed with decaglyceryl monolaurate by sonicating with an ultrasonic probe while cooling to 70° C.

Ciclosporin was dissolved in the mixture during 3 minutes and the warm solution was filtered through a filter having absolute particle separability of 5 µm. The composition was filled into hard gelatin capsules in amounts corresponding to 100 mg, 50 mg an 25 mg of the active ingredient, respectively.

The physical stability of the emulsion formed by dispersing the filling of the capsule in water in a weight ratio of 1:50 was demonstrated by a comparison of the particle size as a function of time and the place of evaluation.

Figure 2:
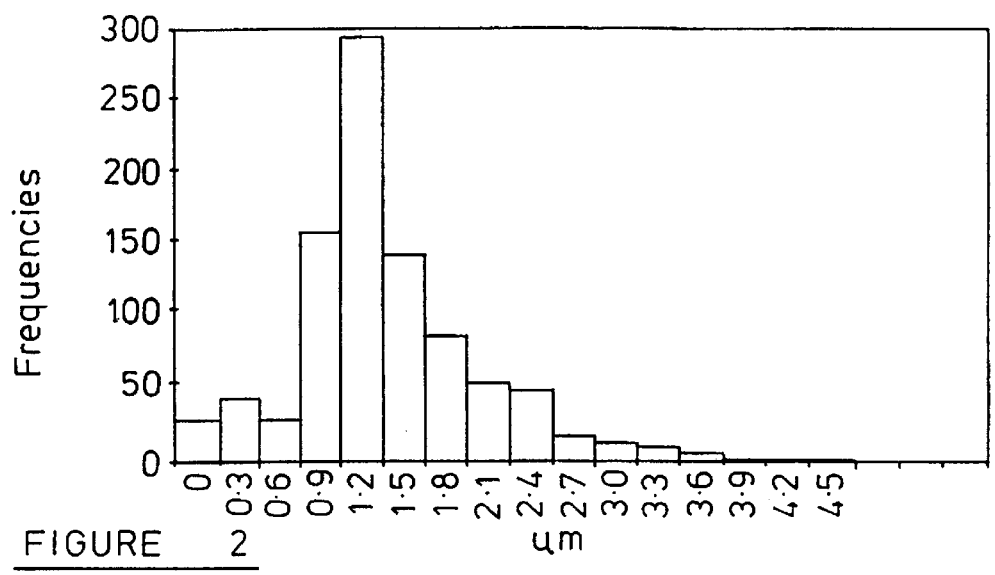
Figure 3:
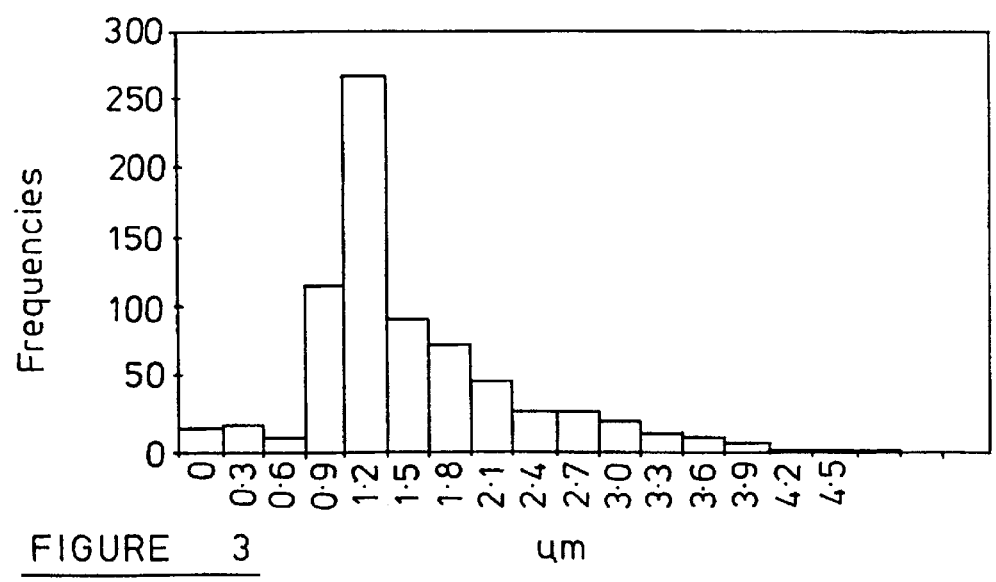

| time [h] | place of evaluation | average size [µg] | minimal size [µg] | maximal size [µm] | histogram |
|---|---|---|---|---|---|
| 0 | middle | 1.68 | 0.18 | 6.38 | FIG. 1 |
| 4 | surface | 1.51 | 0.18 | 4.53 | FIG. 2 |
| 4 | bottom | 1.66 | 0.18 | 5.13 | FIG. 3 |

The histograms of the frequencies and sizes of the particles are shown in FIGS. 1, 2 and 3.

EXAMPLE 3
Starch Capsules

A formulation was prepared from the following ingredients:

| | |
|---|---|
| ciclosporin | 18.00 g |
| tetraglyceryl monostearate | 14.50 g |
| decaglyceryl monomyristate | 67.50 g |

Ciclosporin was dissolved in a melt of tetraglyceryl monostearate and decaglyceryl monomyristate at 70° C.

The solid solution was charged into an extruder at the ambient temperature and pellets were prepared from the extrudate by spheronizing and was filled into bipartite starch capsules.

EXAMPLE 4
Soft Gelatin Capsules

A formulation was prepared from the following ingredients:

| | |
|---|---|
| ciclosporin | 10.00 kg |
| diglyceryl monooleate | 35.00 kg |
| decaglyceryl monolaurate | 55.00 kg |

The diglyceryl monooleate was mixed in a Frymix processing device with decaglyceryl monolaurate at 60° C. Ciclosporin was added and mixing in an evacuated vessel was continued until the ciclosporin dissolved. The warm product was filtered and filled into soft gelatin capsules in amounts corresponding to 25, 50 and 100 mg of ciclosporin.

EXAMPLE 5
Granulate in Sachets

A formulation was prepared from the following ingredients:

| | |
|---|---|
| ciclosporin | 18.00 kg |
| tetraglyceryl tristearate | 14.00 kg |
| decaglyceryl monomyristate | 68.00 kg |
| xylitol | 20.00 kg |

The tetraglyceryl tristearate was mixed in a Frymix with decaglyceryl monomyristate at 70° C. and the ciclosporin was dissolved therein. To this solution was added the crystalline form of xylitol having the melting temperature of 61° C. and the mixture was thoroughly mixed. The cooled mixture was granulated and filled into sachets 2 g each (=300 mg of ciclosporin). The contents of the sachet were stirred into 50 ml of water before drinking.

What is claimed is:

1. A pharmaceutical composition for internal use, comprising:
    10% to 25% by weight of a cyclosporin; and
    a carrier comprising,
    (i) one or more partial esters of $C_{16}$ to $C_{22}$ fatty acids with a glycerol derivative selected from the group consisting of diglycerol to decaglycerol and,
    (ii) one or more partial esters of $C_8$ to $C_{16}$ fatty acids with a glvcerol derivative selected from the group consisting of pentaglycerol to pentadecaglycerol in mutual weight ratios (i):(ii) of 1:1 to 1:5.

2. A composition as claimed in claim 1, wherein the active cyclosporin is selected from the group consisting of [NVa]$^2$-ciclosporin, [Melle]$^4$-ciclosporin and [3'-0-acylMeBml]$^1$-ciclospor.

3. A composition as claimed in claim 1, wherein the glycerol derivatives are selected from the group consisting of diglycerol, triglycerol, tetraglycerol, pentaglycerol, hexaglycerol, heptaglycerol, octaglycerol, nonaglycerol, decaglycerol, and pentadecaglycerol.

4. A composition as claimed in claim 1, wherein the component (i) is selected from the group consisting of diglyceryl monooleate, triglyceryl monooleate, tetraglyceryl monostearate, tetraglyceryl monooleate, decaglyceryl trioleate, decaglyceryl tristearate, and decaglyceryl pentaoleate.

5. A composition as claimed in claim 1, wherein the component (ii) is selected from the group consisting of hexaglyceryl monolaurate, hexaglyceryl monococoate, hexaglyceryl monomyristate, decaglyceryl monolaurate, and decaglyceryl monomyristate.

6. A composition as claimed in claim 1, wherein component (i) is selected from the group consisting of diglyceryl monooleate, diglyceryl dioleate and triglyceryl monooleate and compound (ii) is selected from the group consisting of hexaglyceryl to decaglyceryl monolaurate.

7. A composition as claimed in claim 1, comprising a shape-specific or shape-non-specific dosage form with a nominal content of 10 mg to 300 mg of the active ingredient per dose.

8. A composition as claimed in claim 1, wherein the dosage form is a liquid or easy melting filling of the active ingredient in the carrier, disposed in bipartite gelatin or starch capsules.

9. A composition as claimed in claim 1, further comprising additional adjuvants.

* * * * *